(12) United States Patent
Rashid

(10) Patent No.: US 11,033,423 B2
(45) Date of Patent: *Jun. 15, 2021

(54) FLUENCY AID

(71) Applicant: Cirrus Logic International Semiconductor Ltd., Edinburgh (GB)

(72) Inventor: Tahir Rashid, Tewkesbury (GB)

(73) Assignee: Cirrus Logic, Inc., Austin, TX (US)

( * ) Notice: Subject to any disclaimer, the term of this patent is extended or adjusted under 35 U.S.C. 154(b) by 207 days.

This patent is subject to a terminal disclaimer.

(21) Appl. No.: 16/259,425

(22) Filed: Jan. 28, 2019

(65) Prior Publication Data

US 2019/0231584 A1 Aug. 1, 2019

Related U.S. Application Data

(60) Provisional application No. 62/624,414, filed on Jan. 31, 2018.

(30) Foreign Application Priority Data

Mar. 15, 2018 (GB) ...................................... 1804166

(51) Int. Cl.

| | |
|---|---|
| *A61F 5/58* | (2006.01) |
| *G09B 19/04* | (2006.01) |
| *G10L 25/78* | (2013.01) |
| *G10L 21/0208* | (2013.01) |
| *G10L 21/003* | (2013.01) |
| G10L 21/057 | (2013.01) |
| G10L 21/00 | (2013.01) |

(52) U.S. Cl.
CPC ................ *A61F 5/58* (2013.01); *G09B 19/04* (2013.01); *G10L 21/003* (2013.01); *G10L 21/0208* (2013.01); *G10L 25/78* (2013.01); *G10L 21/00* (2013.01); *G10L 2021/0575* (2013.01); *G10L 2025/783* (2013.01)

(58) Field of Classification Search
CPC .... A61F 5/58; G10L 2021/0575; G10L 21/00
See application file for complete search history.

(56) References Cited

U.S. PATENT DOCUMENTS

| | | | | |
|---|---|---|---|---|
| 5,794,203 | A * | 8/1998 | Kehoe ....................... | A61F 5/58 704/271 |
| 2011/0257464 | A1 * | 10/2011 | Kehoe ....................... | A61F 5/58 600/23 |
| 2012/0033551 | A1 * | 2/2012 | Liao ........................ | H04W 4/70 370/230 |

FOREIGN PATENT DOCUMENTS

| | | | |
|---|---|---|---|
| WO | 200224126 A2 | 3/2002 | |
| WO | WO-2004032816 A2 * | 4/2004 | ........... H04R 25/353 |

OTHER PUBLICATIONS

Combined Search and Examination Report under Sections 17 and 18(3), UKIPO, Application No. GB1804166.5, dated Sep. 17, 2018.

* cited by examiner

*Primary Examiner* — Feng-Tzer Tzeng
(74) *Attorney, Agent, or Firm* — Jackson Walker L.L.P.

(57) ABSTRACT

According to one or more examples of the present disclosure there is provided a fluency aid comprising: an altered auditory feedback, AAF, generator operable to receive an input signal derived from speech of a user and to apply a predefined variation to the input signal in order to generate a feedback signal for providing altered auditory feedback to the user, wherein the AAF generator is further operable to automatically change a property of the variation that is applied to the input signal.

16 Claims, 3 Drawing Sheets

FLUENCY AID

The present disclosure claims priority to U.S. Provisional Patent Application Ser. No. 62/624,414, filed Jan. 31, 2018, and United Kingdom Patent Application No. 1804166.5, filed Mar. 15, 2018, each of which is incorporated by reference herein in its entirety.

TECHNICAL FIELD

The present disclosure relates to a fluency aid, and in particular to a fluency aid for use by persons suffering from a stammer or other speech-related conditions to aid fluency of speaking.

BACKGROUND

Stammering affects about 1-3% of the world's population. From historical records available it is suggested that the condition has always affected 1-3% of the population and is agnostic of race, religion, wealth, and upbringing. Many with the condition are misjudged by the way they talk and as a result many are treated differently in society and may fail to fulfil their potential. The situation can be particularly difficult for children and young adults who may be bullied or ridiculed at school and may find themselves withdrawing from society at a time when they should be finding their place in the world. The condition leaves many feeling anxious and isolated.

There are a number of known auditory effects that can help alleviate stammering. Electronic devices have in the past been created to utilise these effects to help give stammerers greater fluency. Many of these devices are large and cumbersome and cannot be used without attracting further ridicule. More discrete devices still resemble medical devices and their cost puts them out of the reach of most stammerers.

Stammering and stuttering refer to the same condition, with the term stammer being used more in the UK and stutter being used more in the USA. The exact cause of stammering is unknown although it is now generally accepted that it is the result of the brain's neural circuits that control speech having been 'mis-wired'.

Altered Auditory Feedback is used to help improve fluency in people who have medical conditions that effect speech such as Stammering and Parkinson's Disease. For many people who use AAF, their brain can soon learn the trick that is being played on it and will adapt so that the therapy becomes less effective over time. It is therefore desirable to determine a way to alter the AAF in a manner that prevents the brain from adapting and so prolongs the beneficial effects of the AAF.

STATEMENTS OF INVENTION

According to an example of a first aspect of the present disclosure there is provided a fluency aid comprising: an altered auditory feedback, AAF, generator operable to receive an input signal derived from speech of a user and to apply a predefined variation to the input signal in order to generate a feedback signal for providing altered auditory feedback to the user, wherein the AAF generator is further operable to automatically change a property of the variation that is applied to the input signal.

Altered Auditory Feedback is a technique for changing the information fed back to a person (for example a user of the fluency aid) in order to change or mask the person's perception of their own speech. In accordance with this example, the AAF generator is operable to receive an input signal, which is derived from the user's voice (speech). The AAF generator is then operable to generate a feedback signal by applying a variation to the input signal. Specific examples relating to the nature of the variation will be described later. The generated feedback signal may then be output from the AAF generator and used to provide altered auditory feedback to the user. The AAF generator is operable to automatically change a property of the variation applied to the input signal, so that the altered auditory feedback that is provided to the user changes over time.

A user's brain can often quickly adapt to the "trick" being played on it, i.e. the effectiveness of the techniques used to increase fluency can be diminished over time. Therefore, it can be beneficial to combine multiple feedback techniques or to change between multiple feedback techniques in order to keep the brain from adapting and to further prolong the user's fluency. In an example, a series of different techniques may be automatically applied at random so that the user's brain cannot adapt.

Altered Auditory Feedback (AAF) may include for example: Delayed Auditory Feedback (DAF) and/or Frequency Altered Feedback (FAF). These techniques will be further described later. Other forms of AAF are also envisaged. A system which enables the application of a sequence of different forms of AAF may provide a number of advantages that are seen in the overall versatility and effectiveness of the fluency aid. Embodiments of the present examples may be beneficially applicable and/or useful for people suffering from a broader range of speech disorders or stammers.

Preferably, in accordance with one or more examples, the change in a property of the variation comprises a change in the type of variation or a change in at least one parameter of the variation.

As mentioned above, Altered Auditory Feedback (AAF) may include for example: Delayed Auditory Feedback (DAF) and/or Frequency Altered Feedback (FAF). An example of a change in the type of variation may therefore be to change between DAF and FAF. An example of a change in a parameter of the variation may for example be to change a delay time in DAF or change a frequency shift in FAF. Any of these may be considered to be a change a property of the variation.

In accordance with one or more examples, the automatic change is triggered at random. Alternatively, the automatic change may be triggered after an amount of time having elapsed.

Triggering the automatic change to occur at random is potentially advantageous in that the user's brain is less likely to adapt, or learn, to compensate for the AAF or any specific pattern of the change. Some users may achieve equal success by changing the property of the variation based on a timer, so that the AAF generator may apply the automatic change at predetermined intervals.

Preferably, the AAF is a delayed auditory feedback, DAF, and/or a frequency altered feedback, FAF.

Delayed Auditory Feedback (DAF) refers to a technique whereby the speaker's voice is delayed before being presented to the speaker's ears. The level of improvement from stammering to fluency varies from user to user as does the long term effect. In cases where the user demonstrates a decreased effectiveness, altering the delay time has been reported to restore the effectiveness of DAF. The duration of the delay may for example lie in the range of 50-250 ms.

Frequency Altered Feedback (FAF) refers to a technique whereby the user's voice is shifted in frequency before being fed back to the user's ears. It is therefore also referred to as Frequency Shift Feedback (FSF). One approach is to shift the user's voice down one octave. The effectiveness of FAF on reducing stammering is similar to that of DAF. Some studies suggest FAF produces more normal speech, compared to MAF (described later) which tends to lead to louder speech and DAF which tends to lead to slower speech.

Preferably, changing a property of the variation, in DAF, includes changing a delay (a delay time applied to the input signal) and/or, in FAF, includes changing a frequency (an amount of frequency shift applied to the input signal).

Each user may have a range of effective delay times (delay amounts) for DAF and a range of effective frequency alterations for FAF. Therefore, in order to continue to "trick" the brain and maintain effective reduction in stammering, the variation may be changed within each effective range. As mentioned above, testing has shown DAF to be effective in most users at least when duration of the delay lies in the range of 50-250 ms. An example effective range of frequency shift for FAF is ±5 octaves.

According to one or more examples, the fluency aid may further comprise a switch; wherein a change in the property of the variation is triggered by the switch.

The switch may be any suitable switch for this purpose, for example a user-operated switch. The user may notice a tendency for stammering to continue (start again) after the same AAF is applied for some time and therefore a switch may be provided to actively cause the change to occur. Further changes may then continue to be carried out automatically.

According to one or more examples the AAF generator is further operable to provide masked auditory feedback, MAF, by applying a masking signal to the input signal so as to output a masking sound with the altered auditory feedback provided to the user.

Masked Auditory Feedback (MAF) refers to the use of sound to mask the speaker's own voice. In an example of MAF a masking signal is applied to the input signal so as to be able to feedback to the user a feedback signal having a controllable amount of the input signal and a controllable amount of the masking signal present. The masking sound, which is generated by a sound generator based on the masking signal, may take any suitable form, for example white noise, pink noise, tones and/or music. These forms of masking sound may be selected based on user preference, based on effectiveness at relieving the user from the symptoms of stammering or based on the situation, for example if the user needs to hear people that they are speaking to.

According to one or more examples, the fluency aid may further comprise a voice detector for detecting a voice of a user; wherein the masking sound is faded out following detection of the voice of the user or when the voice of the user is no longer detected.

A voice detector is used to determine when the user begins to speak, in that the voice detector detects the user's voice when speaking. The masking sound is therefore output at least until the voice detector detects the user's voice so that the stammer is reduced or prevented entirely. It may be preferable for the masking sound to continue until the user is finished speaking (when the voice is no longer detected) depending on the nature of the user's stammer.

In an example, the masking sound may be played (output) at an initial volume (loudness) which is reduced over time such that the masking sound becomes gradually quieter. This is advantageous to users who wish to hear the masking sound before beginning to speak, but who wish for the masking sound, and the masking effect, to be reduced over time. A user may therefore choose when to begin speaking based on a volume of the masking sound. As the masking sound is faded, the masking effect becomes reduced. Therefore, a user may prefer to begin speaking when their own voice is only partially masked. The masking sound may the preferably be further faded out, once the user has started speaking, or may be output at a constant loudness from the point at which the user starts speaking (the user's voice is detected).

For some users, it may be preferable that the masking sound is played at a constant, initial volume, which is then gradually reduced once they have started speaking. Since some stammerers only stammer when starting to speak, once they have started speaking the masking sound may be reduced in volume so that they can hear their own voice again. This fading out of the masking sound, once the user begins speaking (once the voice detector detects a voice), allows the user to adjust the volume of their own voice, based on their own auditory feedback, so as to speak normally (at a normal volume).

According to one or more examples, once the masking sound is faded out another variation is applied to the input signal.

Once the masking sound fades out to the point of inaudibility, some users may tend to start stammering again. Therefore, once the masking sound is faded out, either partially or fully, another variation may be applied to forestall further stammering. Further changes may preferably then continue automatically.

Preferably, according to one or more examples, the AAF may be output to both ears of the user.

The efficacy of fluency aid in reducing stammering is further improved by ensuring the altered auditory feedback is output to both ears of the user, rather than just one. This ensure, for example in the case of MAF, that the user can only hear a desired amount of their own voice, which may in fact be none (the user may not be able to hear their own voice at all).

According to one or more examples, the fluency aid may further comprise a pacing device to output an audible sound to the user at regularly timed intervals.

Speaking to a timed rhythm is another method of improving fluency in stammerers. There are many different approaches to speech therapy and if the stammerer is having therapy that relies on timing then this can be a valuable tool and may be used in combination with other forms of therapy. The audible sound may preferably be a click or tone sound.

According to one or more examples, the AAF may be output at a loudness that is selected based on the loudness of speech of the user.

Adjusting the loudness of the feedback to the user beneficially allows the AAF to be effective while avoid becoming a source of distraction or changing the way the user speaks in an undesirable manner, such as encouraging them to raise their voice or shout.

Preferably, the AAF generator is activated upon detection of speech by a user.

By activating the AAF generator when the user is speaking, battery power for mobile device can be saved and unwanted feedback of sounds other than the user's voice can be avoided.

According to an example of a second aspect of the present disclosure there is provided a fluency aid comprising: a feedback signal generator to generate an altered auditory feedback, AAF, signal based on an input signal from a user, wherein the input signal is automatically changed between a first state and a second state by application of one or more variations, wherein the first state is a first varied state and the second state is either a second varied state, different to the first varied state, or is an unvaried state.

The application of one or more variations may be selected from a predefined set of variations.

Optionally, the change between the first state and the second state is instant or gradual.

Application of the change between states in the applied variation may be carried out instantly or gradually depending on the nature of the particular variation being applied. In accordance with an example, if a variation produces a clearly recognisable difference to a user, it may be preferable to apply the variation gradually, such as in FAF, whereas some variations are not as recognisable and may therefore be applied instantly, such as in DAF. In FAF, the feedback may sound different to the user's own voice in that the feedback will be frequency altered. Therefore, gradual application of the frequency shift may be desirable to avoid a clear change when the variation is applied. In DAF, the application of a delay to the input signal may not be readily apparent to the user, and therefore the variation may be applied instantly.

According to an example of a further other aspect there is provided a telephone, headphones, acoustic noise cancelling headphones, smart watch, or other portable device comprising the fluency aid as described above. These and any other wearable devices may include a fluency aid as described above.

BRIEF DESCRIPTION OF DRAWINGS

For a better understanding of the present disclosure, and to show how the same may be carried into effect, reference will now be made, by way of example only, to the accompanying drawings in which.

Throughout this description any features which are similar to features in other figures have been given the same reference numerals.

DETAILED DESCRIPTION

The description below sets forth example fluency aids according to this disclosure. Further examples and implementations will be apparent to those having ordinary skill in the art. Further, those having ordinary skill in the art will recognize that various equivalent techniques may be applied in lieu of, or in conjunction with, the examples discussed below, and all such equivalents should be deemed as being encompassed by the present disclosure.

The arrangements described herein can be implemented in a wide range of devices and systems. However, for ease of explanation, an illustrative example will be described.

Figure 1:
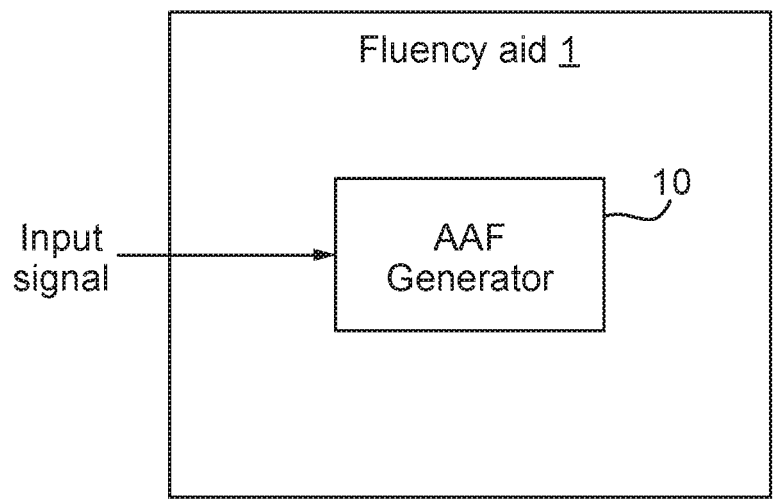
FIG. 1 is an example of a fluency aid according to the present disclosure.

FIG. 1 illustrates a first example of a fluency aid 1 according to the present disclosure. As shown, a fluency aid 1 includes an altered auditory feedback, AAF, generator 10 which receives an input signal derived from speech of a user.

The AAF generator 10 applies a predefined variation to the input signal in order to generate a feedback signal for providing altered auditory feedback to the user. The AAF generator 10 automatically changes a property of the variation that is applied to the input signal.

In more detail, an input signal is received at the AAF generator 10. The input signal is received in a format suitable for manipulation by the AAF generator 10. The input signal may be received as a stream of data, resembling the ongoing speech of the user. The AAF generator 10 is able to apply a variation to the input signal. In a specific example the AAF generator is configured to receive an input signal and to apply a frequency shift (in FAF), for example, to the input signal so that the feedback signal generated resembles a frequency shifted input signal. The frequency shifted input signal may then, as the feedback signal, be used to provide AAF to the user e.g. by passing the feedback signal to a sound generator such as a loudspeaker. According to the present examples, the AAF generator 10, when receiving the input signal and applying the variation, is beneficially operable to automatically change the variation that is applied to the input signal. Thus, the AAF generator may apply a sequence of different variations to the input signal, and each variation may include one or more types of AAF (for example FAF and DAF may be applied together). The order of the sequence may be random or predetermined. For example, the AAF generator 10 may initially apply a frequency shift, as described above, then may apply a different frequency shift (a different shift amount), and then may apply a delay to the input signal, in the feedback signal, as the variation. In this way, a user's brain is less likely to be able to predict, or adapt to, an applied variation, thus prolonging the effect of a reduction in stammering for the user.

In a further example, a user may wish to speak, for example to another person over the telephone or in person, and may find that unaided they have a tendency to experience stammering. The user may therefore use a fluency aid 1 as described above, wherein, when the user speaks, their speech may be picked up by a voice detector, microphone or any other suitable detector. From the speech, an input signal may be derived. The input signal being representative of the user's speech. The fluency aid 1 comprises an AAF generator 10, which is operable to receive the input signal and generate a feedback signal. The feedback signal is preferably based on the input signal, which may be described as a voice signal, wherein one or more types of AAF (variations) have been applied to the input signal. The input signal, being based on a user's voice, may be received at the AAF generator 10 as a data stream (input signal stream), wherein the one or more types of AAF are applied to the stream as each part in the stream is received. The AAF generator 10 is operable to automatically change a property of the variation that is applied to the input signal. Therefore, when receiving the input signal as a stream, the AAF generator is operable to apply one or more variations to the received part of the stream and apply a different variation, in which a property has been changed, to a subsequent part of the stream. Therefore, when the altered auditory feedback is provided to the user, the AAF is also provided as a stream, for example an auditory feedback of their own voice with sequentially applied variations, wherein a property of each sequential variation is changed relative to the preceding variation.

Figure 2:
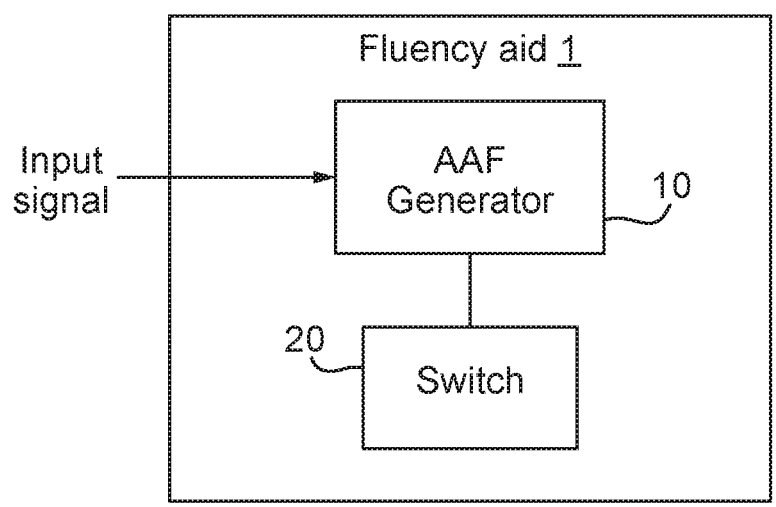
FIG. 2 is an example of a fluency aid according to the present disclosure further comprising a switch.

FIG. 2 illustrates a second example of a fluency aid 1 according to the present disclosure, wherein the fluency aid 1 further includes a switch 20. The switch 20 is used to trigger the change in the property of the variation. The switch 20 may be any suitable switch, such as a user-operated switch and/or a hook-switch.

In an example, the user of the fluency aid 1 as shown in FIG. 2 may notice that the automatic change of the property of the variation, in one instance, may not be applied quickly enough. The application of the change may be random and therefore a single variation may be occasionally continuously applied for a long time. Therefore, if a user notices a tendency to stammer occurring, the user may use the switch 20 to trigger a variation property change.

Figure 3:
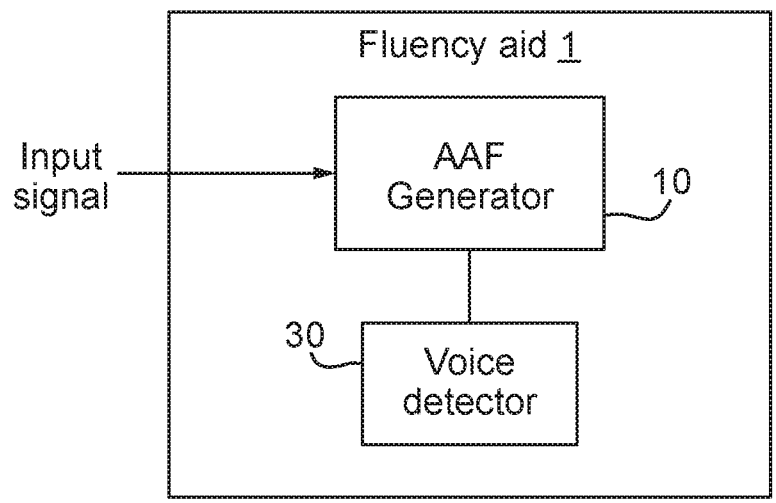
FIG. 3 is an example of a fluency aid according to the present disclosure further comprising a voice detector.

FIG. 3 illustrates a third example of a fluency aid 1 according to the present disclosure, wherein the fluency aid 1 further includes a voice detector 30 operable to detect a voice of a user. The voice detector 30 may for example be useful in the situation where MAF is provided as AAF to the user. In this example, a masking sound is faded out following detection of the voice of the user or when the voice of the user is no longer detected.

The voice detector 30 may operate on the basis of detecting any sound at all or any sound above a threshold level (e.g. a threshold loudness level). Such a threshold may be calibrated based on detected background sound levels. Alternatively, the voice detector 30 may be operable to recognise sounds resembling speech, for example speech patterns, or even a specific user's voice so as to distinguish the user's voice from the voices of other people speaking nearby.

When determining whether the user has started speaking (that a voice is detected), the voice detector 30 may require that speech is detected, in any of the ways described above, for a minimum amount of time. This minimum amount of time (e.g. a minimum amount of speech) may be set as a few seconds of continuous speech or, if the voice detector 30 is able to recognise sounds resembling speech, may be set as one or more spoken words.

The AAF generator 10 is operable to continue generating the masking signal, which in turn leads to the masking sound being output, at least until the voice detector 30 detects the user's voice. Once the user starts speaking, and the voice detector 30 considers the speech to be a detected voice as described above, the AAF generator 10 may either continue to generate the masking signal or may stop generating the masking signal.

The voice detector 30 may for example be a microphone. The voice detector 30 may be comprised as part of the fluency aid 1, as described in the example above, or alternatively may be separate from the fluency aid 1.

Figure 4:
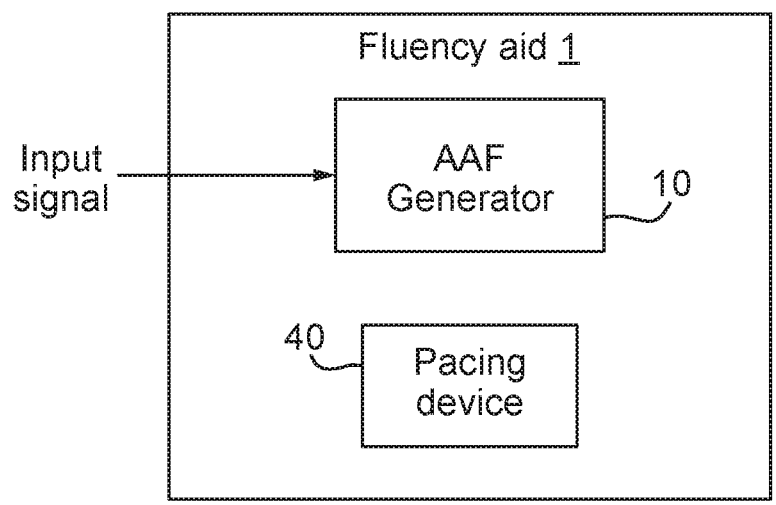
FIG. 4 is an example of a fluency aid according to the present disclosure further comprising a pacing device.

FIG. 4 illustrates a fourth example of a fluency aid 1 according to the present disclosure. As shown, the fluency aid 1 further comprises a pacing device 40 to output an audible sound to the user at regularly timed intervals.

The pacing device 40 may include a speaker or may be included in headphones for generating the audible sound. The pacing device 40 may output the audible sound to the AAF generator 10 so that the audible sound is included in the altered audible feedback, which is output to a user. Alternatively, the audible sound may be output separately from the altered auditory feedback.

In an example, the fluency aid 1, including the pacing device 40, may be used by a stammerer who has found that speaking in time with a regular beat aids fluency of speech. The pacing device 40 is operable to output the regular beat, which is an example of an audible sound, as described above.

Figure 5:
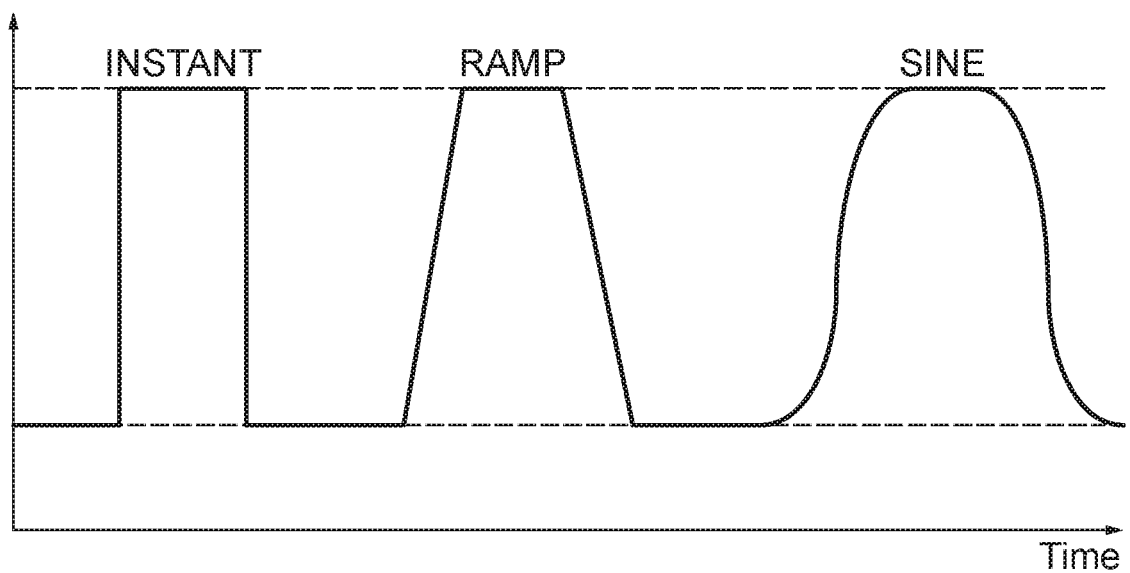
FIG. 5 is a graph showing exemplary forms of different applications of change.

FIG. 5 illustrates an example of how a change of a property of a variation may be applied. FIG. 5 shows three forms of application of change. The first (left-most) form relates to an instant application of change, wherein a property of a variation is instantly applied with no gradation of phasing-in of the newly-applied variation. The second and third forms (middle and right-most) relate to gradual applications of change, specifically ramped and sinusoidal applications of change, respectively.

In the example illustrated in FIG. 5, and in accordance with an example of the second aspect described above, the lower dashed line may for example represent a first state and the upper dashed line may represent a second state, wherein the first state is a first varied state and the second state is either a second varied state, different to the first varied state, or is an unvaried state, and the connecting lines represent the application of the variation to the input signal.

Application of the variations may be carried out instantly or gradually, as shown in FIG. 5, depending on the nature of the one or more variations being applied. In accordance with an example, if a variation produces a clearly recognisable difference to a user, it may be preferable to apply the variation gradually, such as in FAF, whereas some variations are not as recognisable and may therefore be applied instantly, such as in DAF. In FAF, the feedback may sound different to the user's own voice in that the feedback will be frequency altered. Therefore, gradual application of the frequency shift may be desirable to avoid a clear change when the variation is applied. In DAF, the application of a delay to the input signal may not be readily apparent to the user, and therefore the variation may be applied instantly.

Any of the above-described examples may be included in a telephone, headphones, acoustic noise cancelling headphones, smart watch, or other portable or wearable device.

It will be appreciated that features of any of the above aspects and examples may be provided in any combination with the features of any other of the above aspects and examples.

The fluency aid may be at least partly implemented within a speaker housing. The housing may be, e.g., that of a wired or wireless headset, an ear-bud a supra-aural head phone or a speaker portion of a mobile device such as a mobile phone handset. Alternatively, the parts associated with one or more features of the fluency aid may be provided in an apparatus separate from the apparatus that comprises the at least one speaker. For example, the fluency aid may be at least partly implemented within a mobile handset or a "dongle", wherein a wired or wireless connection is provided between the apparatuses. According to one implementation the switch and/or the voice detector are provided in an apparatus that is separate from the apparatus, e.g. headset or ear-bud.

It should be noted that the above-mentioned examples illustrate rather than limit the disclosure, and that those skilled in the art will be able to design many alternative configurations without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope. The features of any dependent claim may be combined with the features of any of the independent claims or other dependent claims.

The invention claimed is:

1. A fluency aid comprising:
   an altered auditory feedback, AAF, generator operable to receive an input signal derived from speech of a user and to apply a predefined variation to the input signal in order to generate a feedback signal for providing altered auditory feedback to the user, wherein:

the AAF generator is further operable to automatically change a property of the variation that is applied to the input signal, wherein the automatic change is triggered at random.

2. The fluency aid according to claim 1, wherein the change in a property of the variation comprises a change in the type of variation or a change in at least one parameter of the variation.

3. The fluency aid according to claim 1, wherein the AAF is a delayed auditory feedback, DAF, and/or a frequency altered feedback, FAF.

4. The fluency aid according to claim 3, wherein changing a property of the variation, in DAF, includes changing a delay in the delayed auditory feedback and/or, in FAF, includes changing a frequency in the frequency altered feedback.

5. The fluency aid according to claim 1, further comprising:
a switch; wherein
a change in the property of the variation is triggered by the switch.

6. The fluency aid according to claim 1, wherein the AAF generator further provides masked auditory feedback, MAF, by applying a masking signal to the input signal so as to output a masking sound with the altered auditory feedback provided to the user.

7. The fluency aid according to claim 6, further comprising:
a voice detector for detecting a voice of a user; wherein
the masking sound is faded out following detection of the voice of the user or when the voice of the user is no longer detected.

8. The fluency aid according to claim 7, wherein once the masking sound is faded out another variation is applied to the input signal.

9. The fluency aid according to claim 1, wherein the AAF is output to both ears of the user.

10. The fluency aid according to claim 1, further comprising:
a pacing device to output an audible sound to the user at regularly timed intervals.

11. The fluency aid according to claim 1, wherein the AAF is output at a loudness based on the loudness of speech of the user.

12. The fluency aid according to claim 1, wherein the AAF generator is activated upon detection of speech by a user.

13. A fluency aid comprising:
a feedback signal generator to generate an altered auditory feedback, AAF, signal based on an input signal from a user, wherein the input signal is automatically changed between a first state and a second state by application of one or more variations, based on a predefined set of variations, wherein:
the first state is a first varied state and the second state is either a second varied state, different to the first varied state, or is an unvaried state, wherein the automatic change is triggered at random.

14. The fluency aid according to claim 13, wherein the change between the first state and the second state is instant or gradual.

15. A telephone, headphones, acoustic noise cancelling headphones, smart watch, or other portable device comprising the fluency aid according to claim 1.

16. A telephone, headphones, acoustic noise cancelling headphones, smart watch, or other portable device comprising the fluency aid according to claim 13.

* * * * *